United States Patent [19]
Rochat

[11] Patent Number: 5,269,924
[45] Date of Patent: Dec. 14, 1993

[54] BLOOD COLLECTING AND FILTERING APPARATUS

[75] Inventor: Jean-Denis Rochat, Mies, Switzerland

[73] Assignee: Elp Rochat, Mies, Switzerland

[21] Appl. No.: 913,009

[22] Filed: Jul. 14, 1992

[30] Foreign Application Priority Data

Jul. 26, 1991 [CH] Switzerland ............... 2249/91

[51] Int. Cl.$^5$ ............... B01D 35/00; A61M 1/00
[52] U.S. Cl. ............... 210/445; 210/416.1; 604/319; 604/409; 604/410
[58] Field of Search ............... 210/232, 416.1, 448, 210/445; 604/319, 320, 321, 406, 408, 409, 410; 422/44, 45, 48

[56] References Cited

U.S. PATENT DOCUMENTS

| 4,346,711 | 8/1982 | Agdanowski et al. | 604/128 |
| 4,466,888 | 8/1984 | Verkaart | 210/232 |
| 4,493,705 | 1/1985 | Gordon et al. | 604/406 |
| 4,943,288 | 7/1990 | Kurtz et al. | 604/319 |

FOREIGN PATENT DOCUMENTS

| 0040427 | 11/1981 | European Pat. Off. |
| 1810801 | 6/1970 | Fed. Rep. of Germany |
| 3328562 | 2/1984 | Fed. Rep. of Germany |
| WO8602844 | 5/1986 | World Int. Prop. O. |
| WO88/10124 | 12/1988 | World Int. Prop. O. |

*Primary Examiner*—Robert A. Dawson
*Assistant Examiner*—Sun Uk Kim
*Attorney, Agent, or Firm*—Young & Thompson

[57] ABSTRACT

A blood collecting and filtering apparatus comprises a container (1) defining with a removably fixed cover (2) a tightly closed enclosure. The cover (2) is provided with an adjustable device (6) for connecting to a reduced pressure system and has a traversing opening (4). A disposable flexible filtration bag (10) is disposed in service position inside said enclosure. The bag has two internal rooms (13, 14) separated the one from the other by a filtering wall (12). The first room (13) is connected to the outside by an inlet pipe (15) for feeding blood to be treated, and the second room (14) is connected to the outside by an outlet pipe (16) for filtered blood. The second room has an opening which is closed by an element (17) made of a material which is permeable to air and impervious to liquids. Both inlet (15) and outlet (16) pipes pass in a tight manner through a plug (21) which in service position closes the traversing opening (4) of the cover (2).

4 Claims, 2 Drawing Sheets

5,269,924

BLOOD COLLECTING AND FILTERING APPARATUS

FIELD OF THE INVENTION

The present invention relates to an apparatus for the recovery and the sterile filtration of per- and post-operative blood, as well as to a disposable flexible filtration bag for this apparatus.

BACKGROUND OF THE INVENTION

This type of apparatus, which works by suction under vacuum, is intended to be used as a rough filtration of the blood, before said blood is introduced in a blood washing apparatus and eventually reinfused into the same patient (auto-transfusion).

Such apparatuses are already known, for example from the U.S. Pat. No. 4,466,888, in which a blood collecting bag is clamped along its peripheral edges between the two parts of a rigid shell. However, such apparatuses have been shown to be practically unusable for collecting post-operative blood, since the tightness of the system is in sufficient once the vacuum line is disconnected. Other types of apparatuses exist, which present drawbacks, either because of the complexity of their use or of their manufacture, or due to a too high cost, or still because they are simply inefficient.

The purpose of the present invention thus consists in providing an apparatus for the collection and the sterile filtration of per- and post-operative blood, which overcomes the drawbacks of the known apparatuses, and which is therefore easy to manufacture and to use, but nevertheless efficient, and particularly whose disposable part is inexpensive.

SUMMARY OF THE INVENTION

The above-mentioned purpose is achieved with the apparatus according to the invention, which comprises a container defining with a removably fixed cover a tightly closed rigid enclosure. The cover is provided with an adjustable device for connection to a reduced pressure line and presents a traversing opening, as well as a disposable flexible filtration bag disposed in service position inside of said enclosure. The bag has two internal rooms separated the one from the other by a filtering wall. A first room is connected to the outside by an inlet pipe, which is fed with blood to be treated. The second room is connected to the outside by an outlet pipe for the filtered blood. The wall of the second room is provided with an opening which is closed by an element made of a air permeable and liquid tight material. Both inlet and outlet pipes respectively pass in a tight manner through a plug closing in service position the traversing opening of the cover.

Another object of the invention consists in a disposable and sterile flexible bag for the collection and the filtration of per- and post-operative blood, which is usable in the apparatus according to the invention, and which comprises two internal rooms separated the one from the other by a filtering wall. A first room is connected to the outside by an inlet pipe, which is fed with blood to be treated, and a second room is connected to the outside by an outlet pipe for the filtered blood. The wall of the second room is provided with an opening closed by an element made of an air permeable and liquid tight material. Both inlet and outlet pipes respectively pass in a tight manner through a plug, intended to close in service position the traversing opening of the cover of the apparatus.

BRIEF DESCRIPTION OF THE DRAWINGS

The annexed drawings show schematically and by way of example an embodiment of the apparatus and of the disposable flexible bag according to the invention.

DETAILED DESCRIPTION OF THE INVENTION

Figure 1:
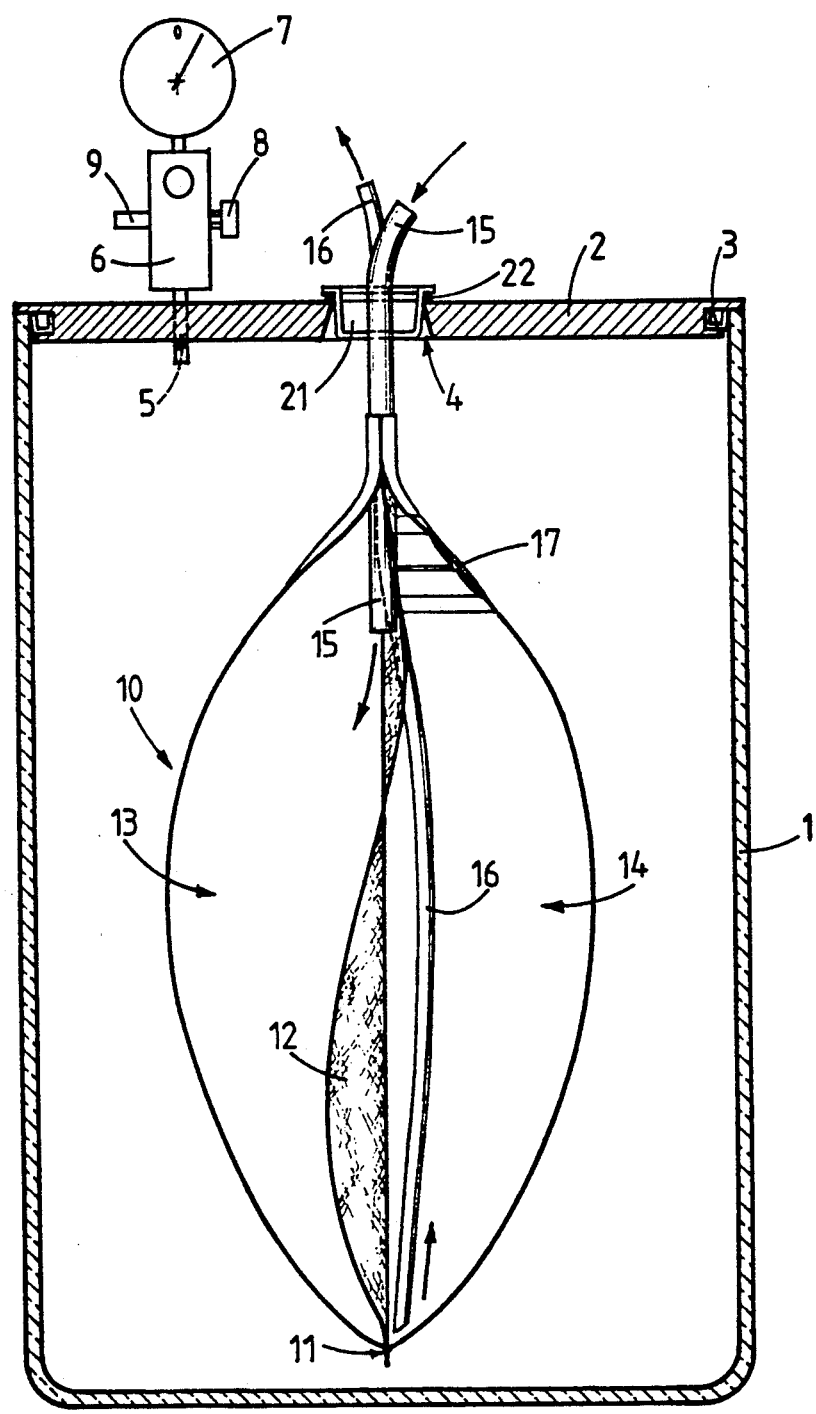
FIG. 1 is a general and partly cross-sectional view thereof in service position.

By reference first to FIG. 1, the apparatus according to the invention comprises a cylindrical container 1 preferably made of glass or of rigid plastic material, whose upper opening may be tightly closed by a rigid cover 2, preferably made of metal, the tightness being obtained by a joint 3, for example a V-shaped silicone joint. The cover 2 has a central opening 4 and a vacuum inlet hole 5. A pressure regulating device 6 is fixedly mounted on this latter hole, said device being provided with a control manometer 7, an adjustment knob 8 and a connection pipe 9. The whole container 1—cover 2—vacuum regulating device 6 constitutes the non-disposable fixed part of the apparatus according to the invention.

Figure 2:
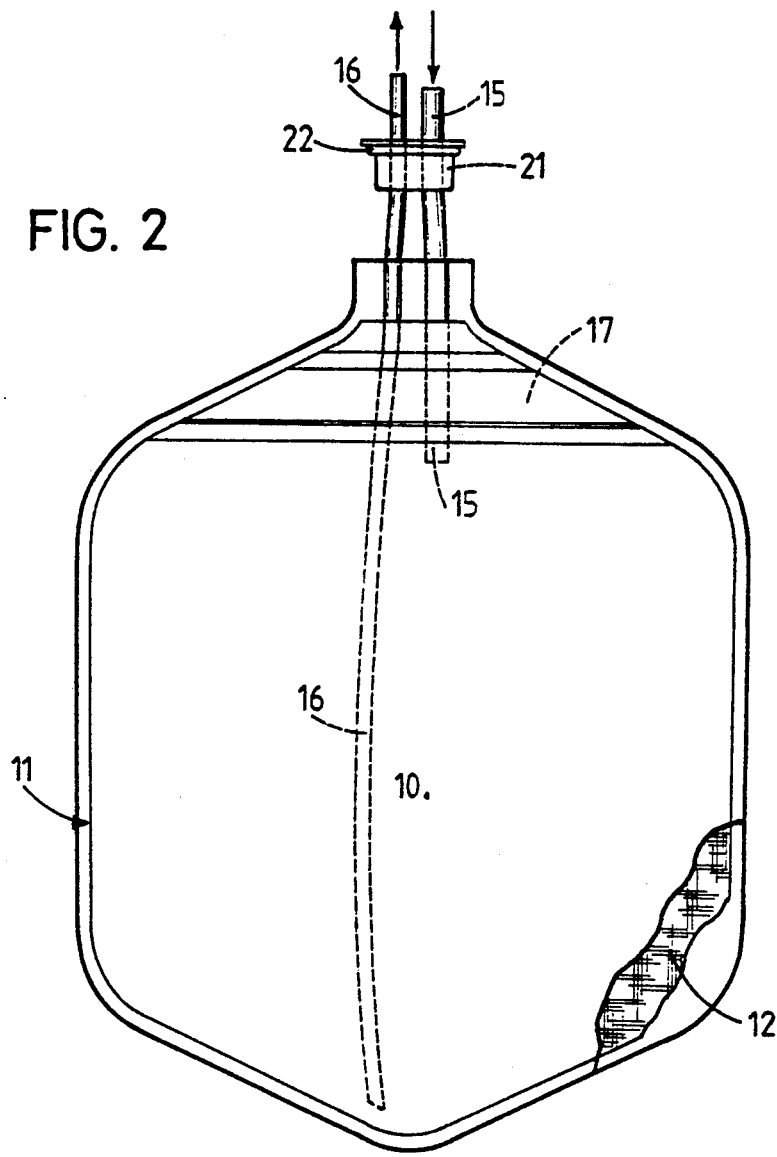
FIG. 2 is a plan view of the disposable flexible bag in out-of-service position.
Figure 3:
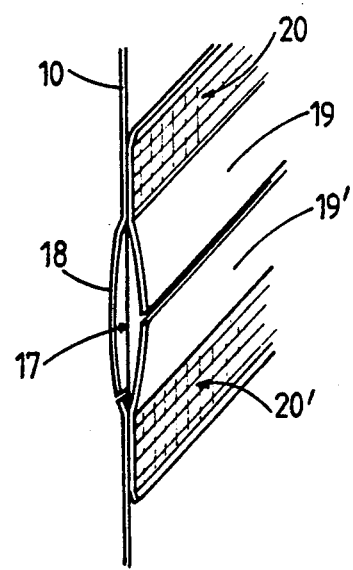
FIG. 3 is a cross-sectional view of a detail of this bag.

As to the disposable part of the apparatus according to the invention, such as it is shown by way of example on FIGS. 1 to 3, it comprises a flexible bag 10, preferably made of PVC, formed by two walls which are flat assembled by their peripheral edges 11. This bag 10 has, when seen in plan, a conical shape at its upper and lower ends, in order to facilitate the introduction thereof into respectively the taking off from the container 1, through the central opening 4 of the cover 2.

During the manufacture of this bag 10, a filtration internal wall 12, whose flat shape is identical to that of the walls of the bag 10, is welded also by its periphery between both edges of both walls. This filtration wall is preferably constituted by a netting made of "Nylon" having meshes between 100 et 1000 microns, preferably about 300 microns, and divides the inside of the bag 10 into two rooms 13,14 of equal volume. Each of these rooms 13,14 is connected to the outside of the bag 10 by means of a flexible pipe 15,16 and each pipe being fixed in a tight manner by welding with the edges 11 of the two walls of the bag.

The first room 13, in which the pipe 15 emerges, is completely tight and is intended to receive the polluted blood to be filtered, for example after operation, that is which contains blood clots, fragments of bones, etc. The blood is sucked into this first room 13 thanks to the putting under reduce pressure (thereafter named "vacuum") of the apparatus according to the invention.

The second room 14 has an opening, for example with an elongated rectangular shape, provided with a band 17 made of a hydrophobic material, that is a material which is impervious to liquids but permeable to the air, and which allows to put this second chamber under the same pressure than the inside of the cylinder 1. The pipe 16 introduced within this second chamber 14 extends to the bottom thereof, this pipe being intended to pump the filtered blood from this room 14 to bring it further for example towards a blood washing apparatus, before being eventually reintroduced into the blood system of the same patient (autotransfusion).

For manufacture reasons essentially, and as shown on FIG. 3, the hydrophobic band 17, for example made of a material of the type "Millipore Filter", is fixed between a portion 18 of the external wall of the bag 10, in which a horizontal passage slot was cut, and two flaps 19,19' made of a plastic material identical to that of the wall 18 (for example of PVC), by means of two horizontal soldered joints 20,20'.

Finally, both flexible pipes 15,16, respectively for the intake into and the outgoing from the bag 10 of the blood, are welded to a plug 21 intended to be introduced in the central opening 4 of the cover 2, this in a tight manner thanks to a circular joint 22.

For the introduction of the disposable flexible bag 10 into the container 1, this bag should be first rolled up around its vertical axis, and then introduced under this rolled shape through the central opening 4 of the cover 2, this introduction being facilitated by the conical shape of the lower part thereof. Then, the plug 21 is fixed into said opening 4 of the cover 2. The apparatus according to the invention is thus ready to work, as long as of course the vacuum regulation device has been connected to an apparatus for providing vacuum (not shown). The polluted blood coming for example from a catheter used by the surgeon is thus introduced by suction into the first room 13 of the bag 10 by means of the pipe 15 and then, always under the action of suction by the putting under vacuum of the apparatus, the blood passes through the filtration netting wall 12 up to the second room 14, and from that second room the blood may be pumped out of the bag 10 by means of the pipe 16. The hydrophobic band 17 of said second room 14 has three uses: it is used for putting under vacuum first the bag 10, and then the overflow indicating device of this second room, the suction being effectively interrupted if the blood level in this second room overpasses the upper level of said band 17. This hydrophobic band also constitutes a sterile bar between the blood content and the outside of the bag.

The present invention thus provides an apparatus for collecting and filtering per- and post-operative blood, which presents several advantages with regards to the known apparatuses:

The fact that the apparatus has a fixed part (non disposable) which comprises all the connections to the vacuum making system allows the user to avoid handlings which are often difficult and tricky. As a matter of fact, when the container 1 and its cover 2 are fixedly connected to the vacuum system, it is sufficient to introduce a flexible bag 10 as indicated above and to tightly fix the plug 21 in the central opening 4 so that this bag is itself put under the same reduce pressure as the container 1. Due to the presence of the hydrophobic band 17 which provides communication between the inside of the container and the inside of said bag, the blood can be sucked by means of the pipe 15, which has been previously connected to another pipe bringing the blood of the patient. The connection of the filtration bag to the vacuum system is thus practically automatic.

As already explained also, the hydrophobic band 17 is used as a control system of the overflow in the room 14 containing the filtered blood.

Thanks to its conception, the apparatus according to the invention offers a much better tightness, and can thus also be used for collecting post-operative blood, more particularly in conditions were the vacuum system should be disconnected, for example during the transportation of the patient, the container 1 being tightly closed and maintaining the vacuum during a sufficiently long period of time.

Contrary to other known apparatuses whose maximum possible volume is lower than 2 lt, the apparatus according to the invention can be made in such a manner so as to receive more significant blood volumes, for example on the order of about 5 lt. This is especially due to the fact that it comprises a rigid cover, for example made of metal, which may thus have a large diameter without any risk of implosion.

Finally the disposable part of the apparatus according to the invention, that is the flexible filtration bag, is not only easy to make use of, but is relatively simple and especially inexpensive to manufacture.

I claim:

1. Blood collecting and filtering apparatus comprising a container defining with a removably fixed cover a tightly closed rigid enclosure, said cover being provided with an adjustable device for connecting to a reduced pressure line and presenting a traversing opening, a disposable flexible filtration bag disposed in service position inside of said enclosure, said bag being constituted by two superimposed walls of plastic material and of a filtration netting fixed between said two walls by welding of peripheral edges thereof, said bag having two internal rooms separated one from the other by said filtration netting, a first room being connected to the outside by an inlet pipe for feeding in blood to be treated, and a second room being connected to the outside by an outlet pipe for filtered blood, said second room having a wall provided with a horizontal rectangular opening in its upper portion, which is closed by a band of an air-permeable and liquid-tight hydrophobic material, said inlet and outlet pipes passing in a tight manner through a plug, which in service position, closes the traversing opening of said cover.

2. Apparatus according to claim 1, further including tightness joints between the cover and the container, and between the plug and the traversing opening of the cover, and wherein said adjustable device for connecting to a vacuum system comprises a member for controlling the pressure and a manometer.

3. A disposable flexible filtration bag for use in a blood collecting and filtering apparatus having a container defining with a removably fixed cover a tightly closed rigid enclosure, said cover being provided with an adjustable device for connecting to a reduced pressure line and presenting a traversing opening, said disposable flexible filtration bag comprising two superimposed walls of plastic material and a filtration netting, said netting being fixed between said two walls by welding of peripheral edges thereof, said bag having two internal rooms separated one from the other by said filtration netting, a first room being connected to the outside by an inlet pipe for feeding in blood to be treated, and a second room being connected to the outside by an outlet pipe for filtered blood, said second room having a wall provided with a horizontal rectangular opening in its upper portion, which is closed by a band of an air-permeable and liquid-tight hydrophobic material, said inlet and outlet pipes passing in a tight manner through a plug, which in service position, closes the traversing opening of said cover.

4. Bag according to claim 3, wherein said hydrophobic band is provided at least on one side of movable flaps of plastic material.

* * * * *